(12) United States Patent
Bauer et al.

(10) Patent No.: US 9,909,073 B2
(45) Date of Patent: *Mar. 6, 2018

(54) PROCESS OF GENERATING A RENEWABLE BIOFUEL FROM A HYDROTREATED STREAM OF CONDENSED OXYGENATES

(71) Applicant: Inaeris Technologies, LLC, Pasadena, TX (US)

(72) Inventors: Lorenz J. Bauer, Pasadena, TX (US); Leslie May, Houston, TX (US); Jeffrey C. Trewella, Kennett Square, PA (US); Maria Magdalena Ramirez Corredores, Houston, TX (US); Christopher Paradise, League City, TX (US); Nicholas Kent, Houston, TX (US)

(73) Assignee: Inaeris Technologies, LLC, Pasadena, TX (US)

( * ) Notice: Subject to any disclaimer, the term of this patent is extended or adjusted under 35 U.S.C. 154(b) by 20 days.

This patent is subject to a terminal disclaimer.

(21) Appl. No.: 14/858,903

(22) Filed: Sep. 18, 2015

(65) Prior Publication Data

US 2016/0010001 A1    Jan. 14, 2016

Related U.S. Application Data

(63) Continuation of application No. 13/843,406, filed on Mar. 15, 2013, now Pat. No. 9,200,209, which is a (Continued)

(51) Int. Cl.
| | | |
|---|---|---|
| C07C 45/45 | (2006.01) | |
| C10G 3/00 | (2006.01) | |
| C10G 45/02 | (2006.01) | |
| C10G 45/04 | (2006.01) | |
| C07C 45/70 | (2006.01) | |

(Continued)

(52) U.S. Cl.
CPC ............... *C10G 3/50* (2013.01); *C07C 45/70* (2013.01); *C07C 45/74* (2013.01); *C10G 3/42* (2013.01); *C10G 3/44* (2013.01); *C10G 45/02* (2013.01); *C10G 45/04* (2013.01); *C10L 1/04* (2013.01); *C10G 2300/1011* (2013.01); *C10G 2400/02* (2013.01); *C10G 2400/04* (2013.01); *C10L 2200/0469* (2013.01); *C10L 2290/02* (2013.01); *C10L 2290/543* (2013.01); *Y02P 30/20* (2015.11)

(58) Field of Classification Search
None
See application file for complete search history.

(56) References Cited

U.S. PATENT DOCUMENTS

| | | | |
|---|---|---|---|
| 2010/0312028 A1* | 12/2010 | Olson | C10L 1/08 585/242 |
| 2013/0036660 A1* | 2/2013 | Woods | C10G 3/42 44/307 |
| 2013/0237728 A1* | 9/2013 | Lotero | C10L 1/04 585/242 |

* cited by examiner

*Primary Examiner* — Philip Louie
(74) *Attorney, Agent, or Firm* — John Wilson Jones; Jones Delflache LLP

(57) ABSTRACT

A renewable fuel may be obtained from a bio-oil containing $C_3$-$C_5$ oxygenates. In a first step, the bio-oil is subjected to a condensation reaction in which the oxygenates undergo a carbon-carbon bond forming reaction to produce a stream containing $C_6$+ oxygenates. In a second step, the stream is hydrotreated to produce $C_6$+ hydrocarbons.

25 Claims, 3 Drawing Sheets

Related U.S. Application Data continuation-in-part of application No. 13/681,145, filed on Nov. 19, 2012, now Pat. No. 9,290,423.

(51) Int. Cl.
*C07C 45/74* (2006.01)
*C10L 1/04* (2006.01)

PROCESS OF GENERATING A RENEWABLE BIOFUEL FROM A HYDROTREATED STREAM OF CONDENSED OXYGENATES

This application is a continuation application of U.S. patent application Ser. No. 13/843,406, filed on Mar. 15, 2013, which is a continuation-in-part application of U.S. application Ser. No. 13/681,145, filed on Nov. 19, 2012, all of which are herein incorporated by reference in their entirety.

FIELD OF THE INVENTION

The invention relates to a process of generating a renewable biofuel from biomass converted liquids containing $C_3$ to $C_5$ oxygenates by first subjecting the $C_3$ to $C_5$ oxygenates to a carbon-carbon bond forming condensation reaction and then hydrotreating the resulting $C_6+$ oxygenates. The condensation and the hydrotreating of the oxygenates may occur in a single reactor.

BACKGROUND OF THE INVENTION

Renewable energy sources, such as biofuels, provide a substitute for fossil fuels and a means of reducing dependence on petroleum oil. In light of its low cost and wide availability, biomass is often used as a feedstock to produce pyrolysis oil (which is relatively soluble in water) or bio-oil which, in turn, is used to produce biofuel.

Many different conversion processes have been developed for converting biomass to bio-oil or pyrolysis oil. Existing biomass conversion processes include, for example, combustion, gasification, slow pyrolysis, fast pyrolysis, liquefaction and enzymatic conversion. Pyrolysis oil is the resultant of thermal non-catalytic treatment of biomass. The thermocatalytic treatment of biomass renders liquid products that spontaneously separate into an aqueous phase and an organic phase. Bio-oil consists of the organic phase. Pyrolysis oil and bio-oil may be processed into transportation fuels as well as into hydrocarbon chemicals and/or specialty chemicals.

While thermolysis processes and other conversion processes produce high yields of such oils, much of the pyrolysis oil and bio-oil produced is of low quality due to the presence of high levels of low molecular weight oxygenates having 5 or less carbon atoms ($C_5-$). Such low MW oxygenates can be in alcohols, aldehydes, ketones, carboxylic acids, glycols, esters, and the like. Those having an isolated carbonyl group include aldehydes and ketones like methyl vinyl ketone and ethyl vinyl ketone.

Such oils thus require secondary upgrading in order to be utilized as drop-in oxygen free transportation fuels due to the high amounts of such oxygenates. A known method for converting oxygenates into hydrocarbons is hydrotreating wherein the stream is contacted with hydrogen under pressure and at moderate temperatures, generally less than 750° F., over a fixed bed reactor.

Transportations fuels predominately contain hydrocarbons having six or more carbon atoms ($C_6+$) (though small amounts of $C_5$ hydrocarbons are present in some gasolines). Thus, hydrocarbons derived by hydrotreating $C_5-$ oxygenates are of little value in transportation fuels. Additionally, hydrotreating $C_5-$ oxygenates consumes valuable hydrogen in the reactor. Thus, the efficiency of secondary upgrading of pyrolysis oil and bio-oil is compromised by the presence of the $C_5-$ oxygenates.

Alternative processes have therefore been sought for enhancing the efficiency in hydrotreating of oils derived from biomass. Processes for enhancing the yield of hydrotreated pyrolysis oil and bio-oil from streams containing $C_5-$ oxygenates, especially $C_3$ to $C_5$ oxygenates, have been sought.

SUMMARY OF THE INVENTION

The invention is drawn to a process for treating pyrolysis oil or bio-oil wherein carbonyl containing $C_3$ oxygenates, $C_4$ oxygenates and $C_5$ oxygenates and mixtures of such oxygenates are subjected to a condensation reaction prior to subjecting the oil to hydrotreatment. The condensation reaction forms carbon-carbon bonds to produce $C_6+$ oxygenates which are subsequently hydrotreated to $C_6+$ hydrocarbons.

In an embodiment, the invention is drawn to a process for treating pyrolysis oil or bio-oil wherein carbonyl containing $C_3$ oxygenates, $C_4$ oxygenates and $C_5$ oxygenates and mixtures of such oxygenates are subjected to a condensation reaction. The condensation reaction forms carbon-carbon bonds to produce $C_6+$ oxygenates. The $C_6+$ hydrocarbons are then hydrotreated to $C_6+$ hydrocarbons.

The yield of hydrotreated oil from the pyrolysis oil stream or bio-oil stream may be enhanced by subjecting the carbonyl containing $C_3-C_5$ oxygenates in a pyrolysis oil or bio-oil stream to a carbon-carbon bond forming condensation reaction and then hydrotreating the resulting condensate(s).

In an embodiment, a renewable biofuel may be produced from a pyrolysis oil or bio-oil feedstream by first subjecting the carbonyl containing $C_3-C_5$ oxygenates in the oil to a carbon-carbon bond forming condensation reaction. The resulting stream is then hydrotreated to produce a hydrotreated feedstream. Hydrotreatment may occur in a separate reactor as the condensation or in the same reactor as the condensation. A renewable biofuel may be rendered from the hydrotreated feedstream. For instance, a renewable fuel may be prepared by combining the hydrotreated stream with a liquid hydrocarbon obtained from a refinery stream.

In another embodiment, a renewable biofuel may be produced from a hydrotreated pyrolysis oil or bio-oil by first feeding the stream to a condensation reactor, such as a distillation column, and then subjecting the $C_3-C_5$ oxygenates in the stream to a carbon-carbon bond forming condensation reaction followed by hydrotreating the resulting condensates. The hydrotreated condensates may then be subjected to fractionation to render a $C_6+$ naphtha fraction having a final boiling point below about 420° F.

In still another embodiment, a renewable biofuel may be produced from biomass by first separating a predominately liquid phase containing $C_3-C_5$ oxygenates from a treated biomass, forming condensates through a carbon-carbon bond forming reaction from the higher MW oxygenate condensates, and then hydrotreating the condensates. The condensation and hydrotreatment may occur in separate reactors or in a single reactor.

In yet another embodiment, the hydrotreated condensates may be subjected to fractionation to render separate hydrocarbon fractions containing (i) $C_5$, $C_6$, $C_7$ and $C_8$ hydrocarbons and (ii) $C_9+$ hydrocarbons.

In addition, transportation fuels may be prepared from the resulting separated hydrocarbon fractions.

In another embodiment, the hydrotreated condensates are separated into a naphtha fraction containing predominately $C_6$, $C_7$, $C_8$, $C_9$, and $C_{10}$ hydrocarbons and a hydrocarbon fraction containing $C_{11}+$ hydrocarbons.

The $C_3$-$C_5$ oxygenates may include carbonyl containing moieties including carboxylic acids, esters, ketones and/or aldehydes.

In an embodiment, the carbon-carbon bond forming condensation reaction consists of a Diels-Alder reaction.

In another embodiment, the carbon-carbon forming condensation reaction consists of an aldol condensation reaction.

In another embodiment, the carbon-carbon forming condensation reaction consists of a Robinson annulation reaction.

In yet another embodiment, condensation of the oxygenates may occur in the presence of a heterogeneous acid catalyst. Preferred heterogeneous acid catalysts may include natural or synthetic zeolites, sulfonated resins (such as sulfonated polystyrene, sulfonated fluoropolymers, sulfonated fluorocopolymers), sulfated zirconia, chlorided alumina, and amorphous SiAl.

In still another embodiment, condensation of the oxygenates may occur in the presence of a basic catalyst. Preferred basic catalysts are those selected from the group consisting of alkaline oxides, alkaline earth metal oxides, Group IIB oxides and Groups IIIB oxides and mixtures thereof. Included within such basic catalysts are MgO, CaO, SrO, BaO, $ZrO_2$, $TiO_2$, CeO and mixtures thereof.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

The yield of $C_6$+ hydrocarbons from pyrolysis oil or bio-oil may be increased by the process defined herein. The process consists of two principal steps. In the first step, low value carbonyl containing $C_3$, $C_4$, and $C_5$ oxygenates within the stream are converted to heavier ($C_6$+) oxygenates in a condensation reaction. In the second step of the process, the heavier oxygenates are hydrotreated to render the $C_6$+ hydrocarbons. The condensation reaction of the $C_3$, $C_4$, and $C_5$ oxygenates to heavier ($C_6$+) oxygenates and the hydrotreatment of the $C_6$+ oxygenates to render $C_6$+ hydrocarbons may occur in separator reactors or within the same reactor.

Figure 1:
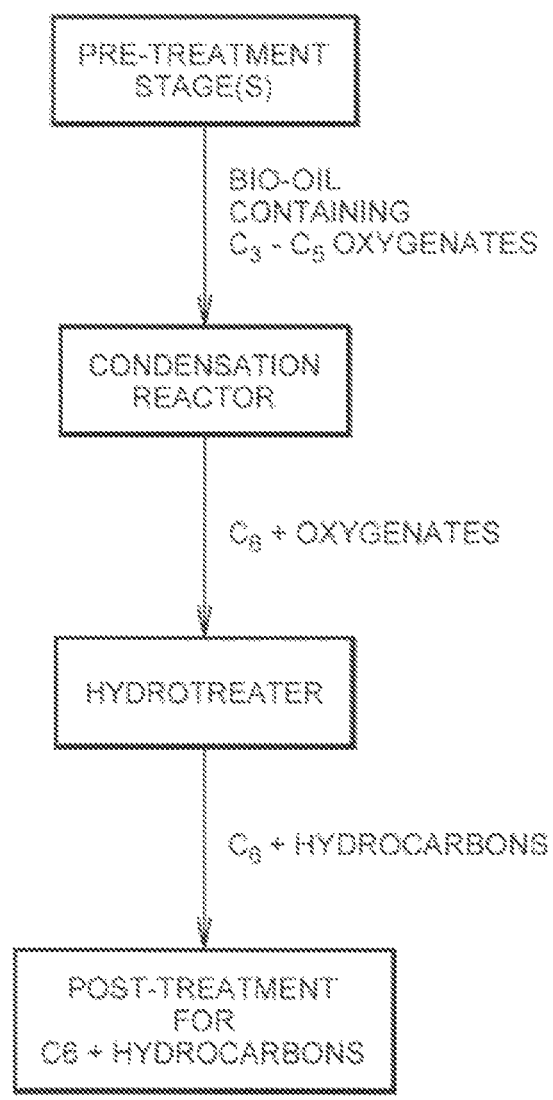
FIG. 1 is a schematic diagram of a representative process defined herein wherein a biomass derived stream is condensed prior to introduction into a hydrotreater.
Figure 3:
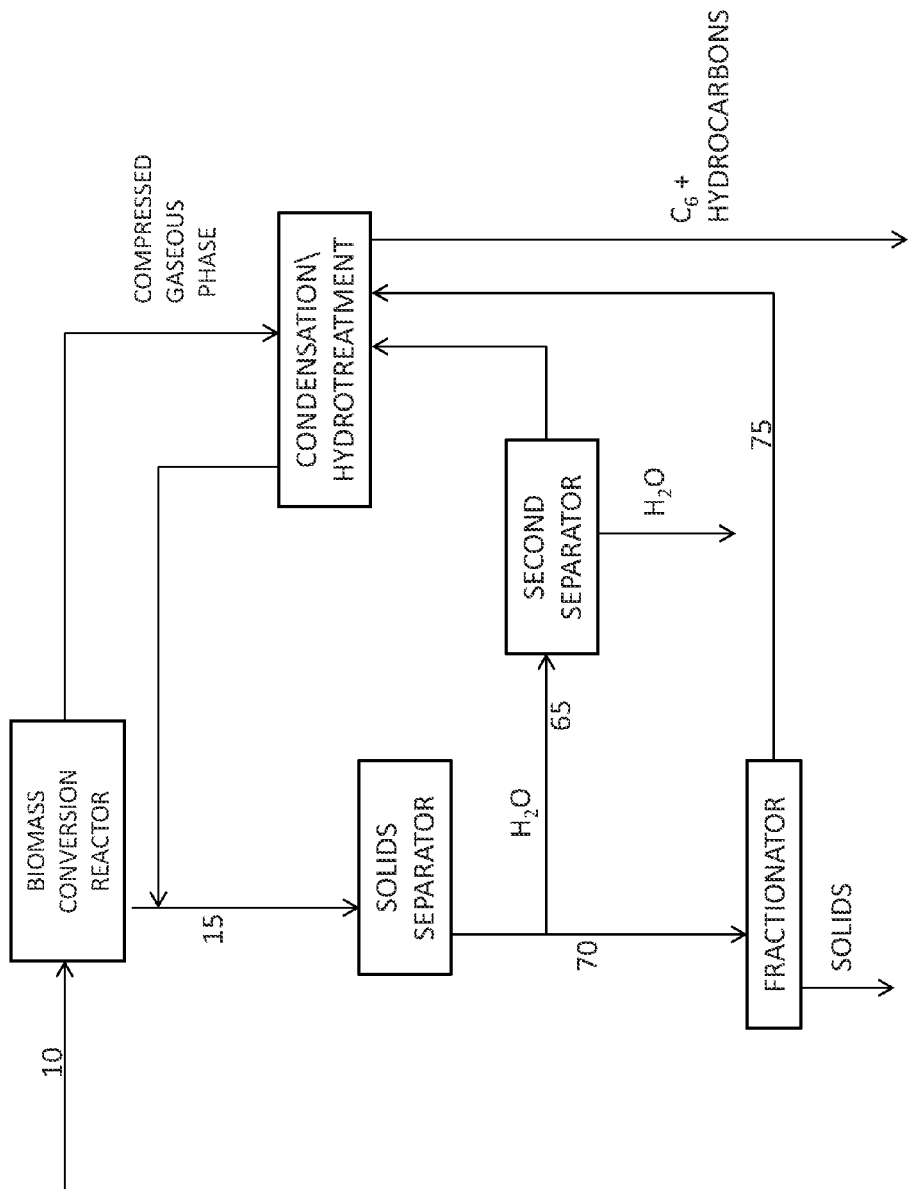
FIG. 3 is a schematic diagram of a representative process using the inventive steps defined herein wherein the condensation reaction and hydrotreatment occurs in a single reactor.

FIG. 1 is a flow diagram wherein bio-oil or pyrolysis oil containing $C_3$-$C_5$ oxygenates is introduced into a condensation reactor prior to treatment of the stream with hydrogen in a hydrotreater. FIG. 3 is a flow diagram showing conversion of the bio-oil or pyrolysis oil into $C_6$+ hydrocarbons in a single reactor. (Shale oil produced by pyrolysis, hydrogenation or thermal dissolution shall be included within the term "pyrolysis oil" as used herein.) The amount of water in the stream introduced into the conversion reactor is typically no greater than 40 volume percent, more typically less than 10 volume percent.

Prior to the condensation reaction, the biomass may be subjected to a pre-treatment operation. After condensation of at least some of the $C_3$-$C_5$ oxygenates, $C_6$+ oxygenates, the condensed bio-oil mixture is subjected to deoxygenation by the introduction of hydrogen. Typically from 90 to about 99.99% of the oxygen is removed from the oxygenates from hydrotreatment.

When separator reactors are used for the condensation reaction and the hydrotreatment, the oxygen typically complexes with hydrogen in the hydrotreater to form water which is decanted from the predominately hydrocarbon hydrotreated oil in the back of the hydrotreater unit. The oil stream exiting the hydrotreater is thereby enriched in $C_6$+ hydrocarbons.

The condensation reaction product consisting of a $C_6$+ oxygenates is produced by a carbon-carbon bond forming reaction between two or more $C_3$-$C_5$ oxygenates. It is possible for any two molecules of carbonyl containing $C_3$-$C_5$ oxygenates to react with each other. Thus, any such $C_3$ oxygenate, for example, may react with one or more such oxygenates selected from $C_3$ oxygenates, $C_4$ oxygenates or $C_5$ oxygenates; any such $C_4$ oxygenate may react with one or more any such oxygenates selected from $C_3$ oxygenates, $C_4$ oxygenates or $C_5$ oxygenates; and any such $C_5$ oxygenate may react with one or more any such oxygenates selected from $C_3$ oxygenates, $C_4$ oxygenates or $C_5$ oxygenates. In addition, any $C_3$ oxygenate, $C_4$ oxygenate or $C_5$ oxygenate may react with one or more oxygenates having carbon content in excess of $C_5$. For example, a $C_3$ oxygenate may react with a $C_7$ oxygenate; a $C_3$ oxygenate may react with a $C_4$ oxygenate and a $C_7$ oxygenate; a $C_3$ oxygenate may react with another a $C_3$ oxygenate, a $C_4$ oxygenate and a $C_7$ oxygenate; etc.

The oxygenates may be converted to higher molecular weight oxygenates in any reactor which affects carbon carbon bond formation. Suitable reactors may include a fixed bed reactor, a continuous stirred tank reactor (CSTR), a distillation column, a catstill (catalytic distillation unit) a stripper, as well as a heat exchanger.

The condensation products may be further processed by hydrotreating to provide renewable transportation fuels.

In a preferred embodiment, the mixture exiting the condensation reactor is deoxygenated in a hydrotreater having a catalytic hydrotreating bed.

Alternatively, the single reactor wherein the condensation reaction and the hydrotreatment both occur contain a catalytic hydrotreating bed as well as the catalysts for condensation of the $C_3$-$C_5$ oxygenates.

The renewable fuel produced in accordance with the process described herein may be blended with a petroleum-derived fuel to produce a blended renewable fuel. For example, the renewable fuel may be blended with a petroleum-derived gasoline in an amount of at least 0.01 to no more than 50 weight percent, including from about 1 to 25 weight percent and further including from about 2 weight percent to 15 percent by weight, of the petroleum-derived gasoline to produce a blended, partially-renewable gasoline. In addition, the renewable fuel may be blended with a petroleum-diesel to produce a blended, partially-renewable diesel fuel in an amount of at least 0.01 to no more than 50 weight percent, including from about 1 to 25 weight percent and further including from about 2 weight percent to 15 percent by weight, of the petroleum-derived diesel. Further, the renewable fuel may be blended with a petroleum-derived fuel oil in an amount of at least 0.01 to no more than 50 weight percent, including from about 1 to 25 weight percent and further including from about 2 weight percent to 15 percent by weight, of the petroleum-derived fuel oil.

The pyrolysis oil or bio-oil containing $C_3$-$C_5$ oxygenates may originate from the treatment of biomass in a biomass conversion reactor. Biomass may be in the form of solid particles. The biomass particles can be fibrous biomass materials comprising cellulose. Examples of suitable cellulose-containing materials include algae, paper waste, and/or cotton linters. In one embodiment, the biomass particles can comprise a lignocellulosic material. Examples of suitable lignocellulosic materials include forestry waste such as wood chips, saw dust, pulping waste, and tree branches; agricultural waste such as corn stover, wheat straw, and bagasse; and/or energy crops such as eucalyptus, switch grass, and coppice. The biomass may be in a solid or finely divided form or may be a liquid. Typically, the water soluble content of the biomass is no greater than about 7 volume percent.

The biomass may be thermocatalytically treated to render bio-oil or may be thermally treated (non-catalytically) to produce pyrolysis oil. Either the bio-oil or the pyrolysis oil may be subjected to any number of conventional treatments prior to being introduced into the reactor where condensation occurs. For instance, the liquid phase of the bio-oil or pyrolysis oil may be separated from the solids in a solids separator. The oil may then be purified, partially purified or non-purified and may be produced within the same plant or facility where the renewable biofuel is prepared or may be produced in a remote location. Further, where two reactors are used, the stream subjected to the condensation reactor may have been produced within the same plant or facility in which the hydrotreater is located. In addition, the biomass may have been treated in the same plant or facility where the renewable biofuel is prepared or produced in a remote location.

Figure 2:
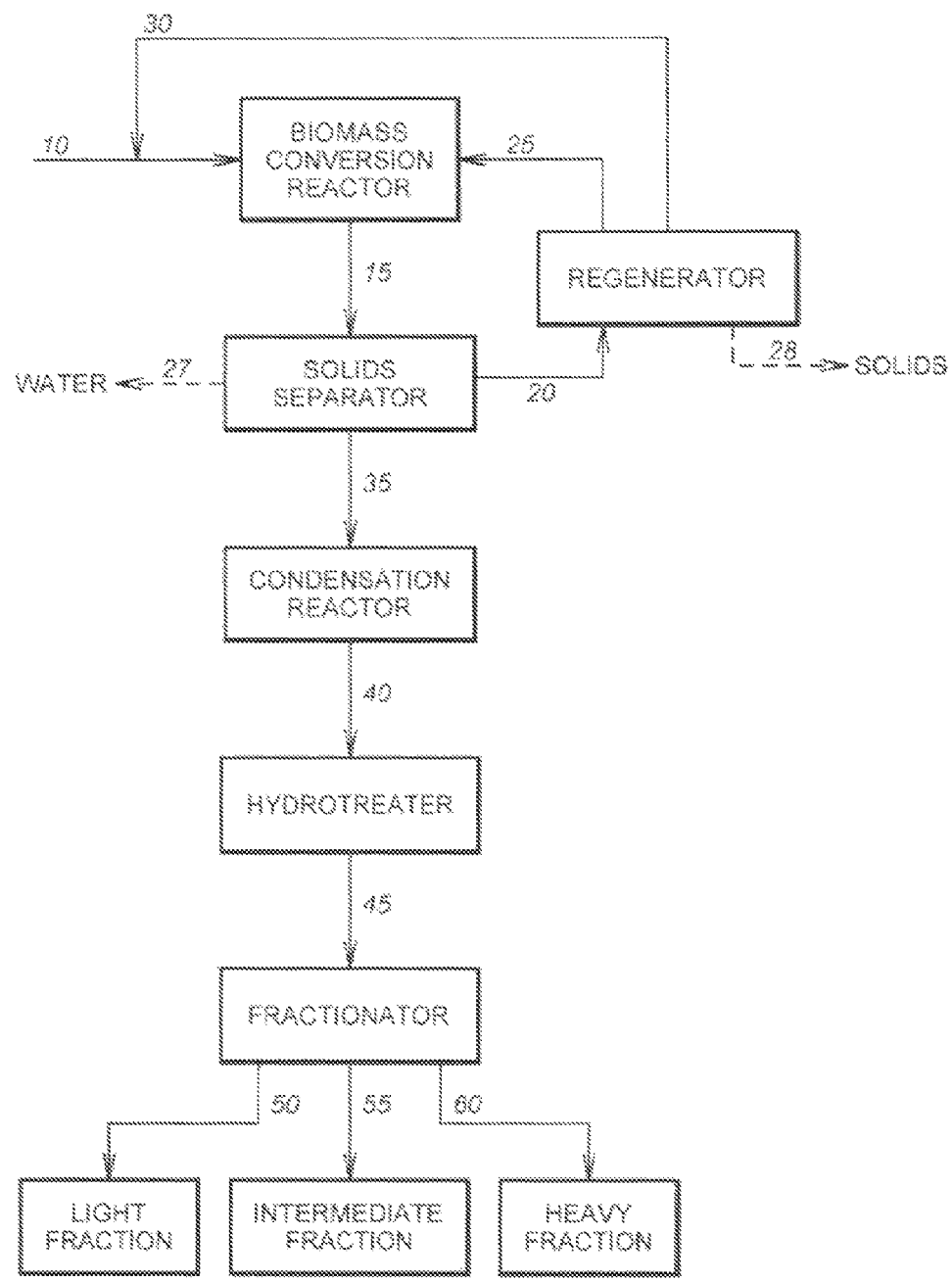
FIG. 2 is a schematic diagram of a representative process using the inventive steps defined herein wherein the condensation reaction and hydrotreatment occurs in separate reactors.

Exemplary treatment stages are illustrated in FIG. 2 and any number of permutations may be used in the process described herein. For example, biomass particles may be prepared from biomass sources and larger particles by techniques such as milling, grinding, pulverization, and the like. The biomass may also be dried by methods known to those skilled in the art.

Referring, for example, to FIG. 2, biomass may be introduced via line 10 into a biomass conversion unit and be subjected to thermal pyrolysis, catalytic gasification, thermocatalytic conversion, hydrothermal pyrolysis, or another biomass conversion process. Biomass conversion unit may include, for example, a fluidized bed reactor, a cyclone reactor, an ablative reactor, or a riser reactor. In a biomass conversion unit, solid biomass particles may be agitated, for example, to reduce the size of particles. Agitation may be facilitated by a gas including one or more of air, steam, flue gas, carbon dioxide, carbon monoxide, hydrogen, and hydrocarbons such as methane. The agitator further be a mill (e.g., ball or hammer mill) or kneader or mixer.

FIG. 2 further shows that effluent from the biomass conversion unit may be introduced into a solids separator via line 15. Suitable separators may include any conventional device capable of separating solids from gas and vapors such as, for example, a cyclone separator or a gas filter.

In addition to the removal of heavy materials and solids, water may be removed during the separation at 27. For instance, during an aldol reaction, water may be removed during separation. There must a density difference between the water and oil in order for the water and oil to separate in the separator.

Solid particles recovered in solids separator may further be introduced into a regenerator via line 20 for regeneration, typically by combustion. After regeneration, at least a portion of the hot regenerated solids may be introduced directly into biomass conversion reactor via line 25. Alternatively or additionally, the hot regenerated solids via line 30 may be combined with biomass prior to introduction of biomass into biomass conversion reactor or may be purged from the regenerator via line 28.

Bio-oil or pyrolysis oil, having the solids removed is then introduced into the condensation reactor via line 35. The bio-oil or pyrolysis oil stream typically has an oxygen content in the range of 10 to 50 weight percent and a high percentage of $C_3$-$C_5$ oxygenates. Typically, from about 1 to about 25 weight percent of the bio-oil contains $C_3$-$C_5$ oxygenates. Such oxygenates may contain carboxylic acids, carboxylic acid ester, ketones (such as methyl vinyl ketone and ethyl vinyl ketone) as well as aldehydes.

The mixture exiting the condensation reactor may then be introduced into the hydrotreating unit via line 40 where the mixture is subjected to deoxygenation by the introduction of hydrogen. Hydrocarbons, water, and other by-products, such as hydrogen sulfide, are formed in the hydrotreatment operation. Prior to introduction into the hydrotreater the mixture exiting the condensation reactor having been enriched in $C_6$+ oxygenates may be subjected to conventional treatments.

Subsequent to producing hydrocarbons in the hydrotreater, the hydrotreated stream may be subjected to any number of conventional post-hydrotreated treatments.

For instance, as illustrated in FIG. 2, all or a portion of the hydrocarbon stream may be introduced into a fractionator via line 45. In the fractionator, at least a portion of the material may be separated through line 50 as light fraction, line 55 as an intermediate fraction, and line 60 as a heavy fraction. The light fraction may have a boiling range below petroleum-derived gasoline and the intermediate fraction may have a boiling range comparable to petroleum-derived gasoline. The heavy fraction may have a boiling range comparable to diesel fuel. For instance, in an embodiment, the light fraction may have a boiling point between from about 150° F. to about 180° F., the intermediate fraction may have a boiling point between from about 180° F. to about 420° F. and the heavy fraction may have a boiling point above 420° F.

FIG. 3 illustrates another embodiment wherein condensation of the $C_3$-$C_5$ oxygenates to $C_5$+ oxygenates and hydrotreating of the $C_5$+ oxygenates to $C_5$+ hydrocarbons occur in a single reactor. Referring to FIG. 3, biomass may be introduced via line 10 into a biomass conversion reactor and treated as set forth above. Effluent from the biomass conversion unit may then be introduced into a solids separator through line 15. In addition to the removal of heavy materials and solids, water may be removed during separation and enter a second separator through line 65. In the second separator, one or more organic streams containing $C_3$-$C_5$ oxygenates may still be separated from the water stream. One or more of these organic streams may then be introduced into the single reactor wherein condensation and hydrotreatment occurs.

All or a portion of the organic stream exiting the solids separator may be fed into a fractionator through line 70. In the fractionator, at least a portion of the stream may be separated as light fraction having the boiling point of naphtha. At least a portion of the naphtha stream may be fed into the single condensation/hydrotreatment reactor via line 75. Further, a portion of the gaseous stream produced in the biomass conversion reactor may be compressed into a liquid stream. This liquid stream containing $C_3$-$C_5$ oxygenates may then be fed into the single condensation/hydrotreatment reactor.

The building of carbon-carbon bonds in the condensation reactor to form $C_5+$ hydrocarbons may progress via an enol or enolate addition to a carbonyl compound. Suitable reactions may include an aldol condensation or Michael addition reaction or a mixture thereof. In addition, the building of carbon-carbon bonds in the condensation reactor may proceed by a cycloaddition reaction wherein two or more independent pi-electron systems form a ring. Suitable cycloaddition reactions may include a Diels Alder reaction, a Robinson annulation reaction as well as mixtures thereof. These reactions can proceed via a base catalyzed anionic reaction mechanism or an acid catalyzed cationic reaction mechanism.

In a preferred embodiment, the cycloaddition reaction is a Diels Alder reaction wherein a conjugated diene or conjugated enone is reacted with a dienophile to render a cyclohexene or a dihydropyran or substituted cyclohexene ring or substituted a dihydropyran. A low molecular weight compound having an electron withdrawing group within the bio-oil or pyrolysis oil may function as the dienophile. Typically, the dienophile is a vinylic ketone or vinylic aldehyde represented by the $C_3$-$C_5$ oxygenates of the bio-oil. A vinylic ketone or vinylic aldehyde can also serve as the conjugated enone. A representative reaction scheme of a Diels-Alder reaction followed by hydrotreating wherein light hydrocarbons are converted to heavy hydrocarbons may be represented as follows:

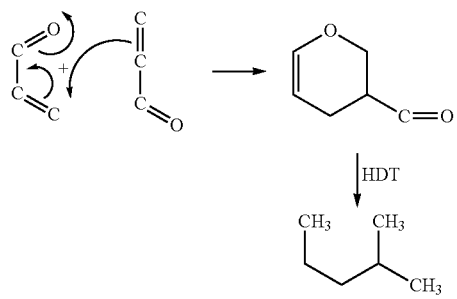

Further, the formation of $C_5+$ hydrocarbons may proceed by an aldol condensation reaction. A representative aldol condensation reaction may be represented by the following schematic pathway wherein an enol or an enolate ion reacts with an aldehyde or a ketone to form either a β-hydroxyaldehyde or a β-hydroxyketone:

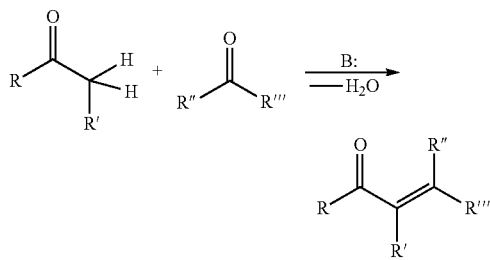

wherein R, R', R" and R'" are each independently selected from the group consisting of hydrogen, hydroxy, $C_1$-$C_8$ alkyl, alkenyl, and cycloalkyl, $C_1$-$C_{10}$ mono- and bicyclic aromatic and heterocyclic moieties (including heterocyclic groups derived from biomass), and carbonyls and carbohydrates such as ethanedione, glyceraldehyde, dihydroxyacetone, aldotetroses, aldopentoses, aldohexoses, ketotetroses, ketopentoses, ketohexoses, etc., provided that both R" and R'" are not hydrogen. The reaction can also proceed via an acid catalyzed cationic reaction mechanism.

The aldol condensation reaction may be a Claisen-Schmidt condensation reaction between a ketone and a carbonyl compound lacking an alpha hydrogen wherein an enolate ion typically is added to the carbonyl group of another, un-ionized reactant.

The reaction of carbonyl containing $C_5$– oxygenates in the condensation reactor may further proceed by a Michael addition wherein the carbonyl oxygenate undergoes a 1,4 addition to an enol or enolate anion.

Further, the $C_5+$ hydrocarbons may be formed by a ring formation reaction such as a Robinson annulation reaction between a ketone containing a α-$CH_2$ group and a α,β-unsaturated carbonyl (like methyl vinyl ketone). In a Robinson annulation reaction, an enolate executes a Michael addition to the α,β-unsaturated carbonyl compound. This is followed by an intramolecular aldol reaction to form the keto alcohol by an aldol ring closure followed by dehydration. Representative Robinson annulations reactions include:

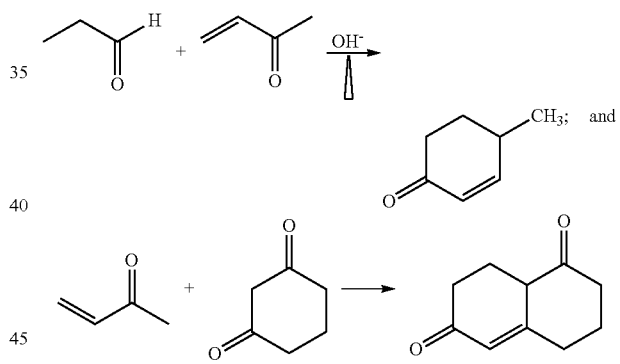

In both of these illustrated reactions, a deprotonated ketone acts as a nucleophile in a Michael reaction on a vinyl ketone to produce a Michael adduct prior to the aldol condensation reaction. The reaction can also proceed via an acid catalyzed cationic reaction mechanism.

Condensation of the $C_3$-$C_5$ oxygenates occurs in the presence of heat. Typically, the $C_3$-$C_5$ oxygenates are subjected to condensation by being heated to a temperature from about 230° F. to about 450° F. The reaction may be promoted and/or facilitated by the presence of a base catalyst or an acid catalyst.

In a preferred embodiment where two reactors are used, condensation occurs by catalytic distillation wherein the catalyst is placed within the condensation reactor in areas where concentrations of reactants are elevated.

The use of base or acid catalysts may enhance the rates of non-concerted carbon-carbon bond forming condensation reactions (such as an aldol or Diels Alder condensation). Suitable base catalysts include alkaline oxides, alkaline earth metal oxides, Group IIB oxides and Groups IIIB oxides as well as mixtures thereof. Exemplary of such catalysts are MgO, CaO, SrO, BaO, $ZrO_2$, $TiO_2$, CeO and mixtures thereof.

Suitable acid catalysts are those homogeneous acid catalysts selected from the group consisting of inorganic acids (such as sulfuric acid, phosphoric acid, hydrochloric acid and nitric acid); trifluoroacetic acid; organic sulfonic acids (such as p-toluene sulfonic acid, benzenesulfonic acid, methanesulfonic acid, trifluoromethanesulfonic acid, 1,1,2,2-tetrafluoroethanesulfonic acid, 1,2,3,2,3,3-hexapropanesulfonic acid); perfluoroalkylsulfonic acids, and combinations thereof. Often, the pKa of the organic acid is less than 4. Also suitable are metal sulfonates, metal sulfates, metal trifluoroacetates, metal triflates, such as bismuth triflate, yttrium triflate, ytterbium triflate, neodymium triflate, lanthanum triflate, scandium triflate, zirconium triflate, and zinc tetrafluoroborate.

In a preferred embodiment, a heterogenous acid catalyst is used such as a natural or synthetic zeolite, sulfonated resin (such as sulfonated polystyrene, sulfonated fluoropolymers, sulfonated fluorocopolymers), sulfated zirconia, chlorided alumina, or amorphous SiAl or a mixture thereof. Exemplary zeolites include those of the ZSM-type, including ZSM-5 (as disclosed in U.S. Pat. No. 4,490,566)) and zeolite beta (disclosed in U.S. Pat. No. 4,490,565).

Perfluorinated ion exchange polymers (PFIEP) containing pendant sulfonic acid, carboxylic acid, or sulfonic acid and carboxylic acid groups may also be used.

In a preferred embodiment, the acid catalyst is a fluorinated sulfonic acid polymers which may be partially or totally converted to the salt form. Such products include those polymers having a perfluorocarbon backbone and a pendant group represented by the formula —$OCF_2CF(CF_3)OCF_2CF_2SO_3X$, wherein X is H, an alkali metal or $NH_4$. Polymers of this type are disclosed in U.S. Pat. No. 3,282,875.

One particularly suitable fluorinated sulfonic acid polymer is Nafion® perfluorinated sulfonic acid polymers of E.I. du Pont de Nemours and Company. Such polymers include those of a tetrafluoroethylene backbone having incorporated perfluorovinyl ether groups terminated with sulfonate groups. Exemplary of such copolymers are Nafion-H and Nafion® Super Acid Catalyst, a bead-form strongly acidic resin which is a copolymer of tetrafluoroethylene and perfluoro-3,6-dioxa-4-methyl-7-octene sulfonyl fluoride, converted to either the proton (H+), or the metal salt form.

Further preferred are sulfonated polymers and copolymers, such as sulfonated polymers of styrene and styrene/divinylbenzene, such as Amberlyst™ of Rohm and Haas, as well as sulfated silicas, aluminas, titania and/or zirconia; sulfuric acid-treated silica, sulfuric acid-treated silica-alumina, acid-treated titania, acid-treated zirconia, heteropolyacids supported on zirconia, heteropolyacids supported on titania, heteropolyacids supported on alumina, heteropolyacids supported on silica, and amorphous SiAl.

Mixtures of two or more acid catalysts may also be used.

When present, the acid catalyst is preferably used in an amount of from about 0.01% to about 10% by weight of the reactants.

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

EXAMPLES

Example 1

A 316L stainless steel double-ended cylinder having a volume of 150 $cm^3$ and capable of withstanding working pressures up to 5000 psig (344 bar) was obtained from the Swagelok Company. The cylinder was filled with ⅔ volume of bio-oil derived from the thermo-catalytic conversion of biomass. Air or nitrogen was introduced into the cylinder to fill the remaining volume. Both ends of the cylinder were plugged and the cylinder was placed into a programmable oven wherein the thermal cycle was controlled by temperatures (room temp to 212° F. @ 5 deg/min, 213° F. to 450° F., 350° F. & 230° F. @ 5 deg/min, 1 hr @ 450° F., 350° F. and 230° F. After the cylinder was cooled to room temperature, it was opened at one end to relieve pressure build-up and the sample removed for analysis. The cylinder was weighed before and after the application of heat and no evidence of weight change was noted. Table 1 depicts the changes in $C_2$-$C_5$ oxygenates and $C_2$-$C_5$ hydrocarbons between the starting bio-oil and the converted bio-oils:

TABLE 1

| Species | Start Oil | $N_2$ - 230° F. | $N_2$ - 350° F. | $N_2$ - 450° F. |
|---|---|---|---|---|
| wt % $C_2$-$C_5$ as Ox's | 4.6 | 3.3 | 3.0 | 2.2 |
| wt % $C_2$-$C_5$ as C's | 3.1 | 2.2 | 2.0 | 1.4 |

Table 2 represents the gas chromatography/mass spectrometry analysis of the starting bio-oil and the heated samples:

TABLE 2

| | Start Oil | $N_2$ - 230° F. | $N_2$ - 350° F. | $N_2$ - 450° F. |
|---|---|---|---|---|
| Oxygenates | | | | |
| Furans | 1.91 | 1.80 | 1.48 | 1.57 |
| Aldehydes | 1.15 | 0.63 | 0.41 | 0.53 |
| Ketones | 3.35 | 2.62 | 2.50 | 1.51 |
| Carboxylic Acids | 0.33 | 0.59 | 0.88 | 0.76 |
| Phenols | 16.06 | 15.80 | 15.48 | 14.97 |
| Indenols | 1.17 | 0.83 | 0.21 | 0.08 |
| Diols | 2.59 | 2.50 | 1.65 | 1.35 |
| Naphthols | 0.43 | 0.28 | 0.21 | 0.24 |
| Hydrocarbons | | | | |
| BTEX | 4.51 | 4.48 | 4.38 | 4.04 |
| Other Polyaromatics | 0.60 | 0.55 | 0.52 | 0.54 |
| Other Alkyl Benzenes | 1.32 | 1.32 | 1.16 | 1.20 |
| Indenes | 1.65 | 1.57 | 1.26 | 1.32 |
| Indanes | 0.17 | 0.19 | 0.18 | 0.18 |
| Naphthalenes | 1.09 | 1.11 | 1.04 | 1.15 |

The majority of ketones, aldehydes and carboxylic acids in Table 2 were $C_3$-$C_5$ oxygenates. Tables 1 and 2 illustrate the decrease in $C_3$-$C_5$ oxygenates in the condensation reactor product after heat treatment. In contrast, the other compound classes were essentially unaffected by treatment in the condensation reactor.

Example 2

A double-ended cylinder described in Example 1 was filled with ⅔ volume of a naphtha fuel stream. Nitrogen was introduced into the cylinder to fill the remaining volume. Both ends of the cylinder were plugged and the cylinder was placed into a programmable oven wherein the thermal cycle was controlled from 213° F. to 450° F. @ 5 deg/min and then 1 hr @ 450° F. After the cylinder was cooled to room temperature, it was opened at one end to relieve pressure build-up and the sample removed for analysis. The cylinder was weighed before and after the application of heat and no evidence of weight change was noted. The gc/ms data of the starting naphtha and the naphtha following completion of heating is set forth in Table 3. The majority of ketones, aldehydes and carboxylic acids in Table 3 were $C_3$-$C_5$ oxygenates. Table 3 illustrate the decrease in $C_3$-$C_5$ oxygenates in the condensation reactor after heat treatment.

TABLE 3

|  | Start Naphtha | Reacted Naphtha |
|---|---|---|
| Oxygenates: | | |
| Aldehydes | 2.13 | 1.17 |
| Furans | 1.51 | 1.30 |
| Ketones | 11.90 | 9.10 |
| Carboxylic Acids | 0.21 | 0.30 |
| Phenols | 1.67 | 1.27 |
| Hydrocarbons: | | |
| BTEX | 64.32 | 64.51 |
| Other Benzenes/Toluenes | 7.21 | 5.14 |
| Indenes | 1.05 | 0.74 |
| Indanes | 0.58 | 0.46 |
| Naphthalenes | 0.14 | 0.11 |

From the foregoing, it will be observed that numerous variations and modifications may be effected without departing from the true spirit and scope of the novel concepts of the invention.

What is claimed is:

1. A process for producing a renewable biofuel from liquid bio-oil or liquid pyrolysis oil, the process comprising:
   (a) subjecting a liquid bio-oil or pyrolysis oil feedstream containing carbonyl oxygenates to a carbon-carbon bond forming condensation reaction to form $C_6$+ enriched condensates, wherein the carbon-carbon bond forming condensation reaction comprises an enol or enolate addition to a carbonyl compound, and wherein the oxygenates are selected from the group consisting of $C_3$ oxygenates, $C_4$ oxygenates, $C_5$ oxygenates and mixtures thereof and further wherein the $C_3$ oxygenates, $C_4$ oxygenates and $C_5$ oxygenates are selected from the group consisting of carboxylic acids, carboxylic acid esters, ketones and aldehydes;
   (b) contacting the bio-oil or pyrolysis oil containing condensates of step (a) with hydrogen and hydrotreating the condensates to form a hydrotreated bio-oil or pyrolysis oil comprising $C_6$+ hydrocarbons; and
   (c) fractionating the hydrotreated bio-oil or pyrolysis oil to obtain a $C_6$+ renewable biofuel,
wherein the condensation reaction in step (a) and the hydrotreating in step (b) occurs in a single reactor.

2. The process of claim 1, wherein prior to step (a):
   (i) biomass is converted in a biomass conversion reactor into gaseous, liquid and solid components;
   (ii) the gaseous components and solid components are separated from the liquid components;
   (iii) the liquid components are separated into an aqueous phase and an organic stream containing $C_3$-$C_5$ oxygenates; and
   (iv) the aqueous phase is then separated into another organic stream containing $C_3$-$C_5$ oxygenates.

3. The process of claim 1, wherein the condensation reaction is an aldol condensation.

4. The process of claim 1, wherein the renewable biofuel is produced from liquid bio-oil.

5. A process for producing a renewable biofuel from a liquid bio-oil or pyrolysis oil, the process comprising:
   (a) subjecting a liquid bio-oil or pyrolysis oil feedstream to a separation in a fractionator to produce a stream having the boiling point of naphtha;
   (b) subjecting the naphtha stream and at least a portion of the liquid bio-oil or pyrolysis oil containing carbonyl oxygenates to a carbon-carbon bond forming condensation reaction to form $C_6$+ enriched condensates, wherein the oxygenates are selected from the group consisting of $C_3$ oxygenates, $C_4$ oxygenates and $C_5$ oxygenates and mixtures thereof;
   (c) contacting the bio-oil or pyrolysis oil containing condensates of step (a) with hydrogen and hydrotreating the condensates to form a hydrotreated feedstream; and
   (d) fractionating the hydrotreated feedstream to obtain a $C_6$+ biofuel,
wherein the carbon-carbon forming condensation reaction in step (a) and the hydrotreating in step (b) occurs in a single reactor.

6. The process of claim 5, wherein prior to step (a):
   (i) biomass is converted in a biomass conversion reactor into gaseous, liquid and solid components;
   (ii) the gaseous components and solid components are separated from the liquid components;
   (iii) the liquid components are separated into an aqueous phase and an organic stream containing $C_3$-$C_5$ oxygenates; and
   (iv) the aqueous phase is then separated into another organic stream containing $C_3$-$C_5$ oxygenates.

7. The process of claim 5, wherein condensation occurs in the single reactor in the presence of a heterogeneous acid catalyst.

8. The process of claim 7, wherein the heterogeneous acid catalyst is selected from the group consisting of organic sulfonic acids; perfluoroalkylsulfonic acids; zeolites; sulfated transition metal oxides, and perfluorinated ion exchange polymers containing pendant sulfonic acid, carboxylic acid, or sulfonic acid groups; sulfonated copolymers of styrene and divinylbenzene; sulfated silicas, aluminas, titania and/or zirconia; and amorphous SiAl and mixtures thereof.

9. The process of claim 8, wherein the heterogeneous acid catalyst is selected from the group consisting of ZSM-type zeolites, zeolite beta, sulfonated fluoropolymers or copolymers, sulfated zirconia and amorphous SiAl.

10. The process of claim 7, wherein the heterogeneous catalyst is a zeolite beta.

11. The process of claim 5, wherein condensation occurs in the presence of a basic catalyst selected from the group consisting of alkaline oxides, alkaline earth metal oxides, Group IIB oxides and Groups IIIB oxides and mixtures thereof.

12. The process of claim 11, wherein the basic catalyst is selected from the group consisting of MgO, CaO, SrO, BaO, $ZrO_2$, $TiO_2$, CeO and mixtures thereof.

13. The process of claim 11, wherein the basic catalyst is a supported catalyst.

14. The process of claim 5, wherein the $C_3$ oxygenates, $C_4$ oxygenates and $C_5$ oxygenates are selected from the group consisting of carboxylic acids, carboxylic acid esters, ketones and aldehydes.

15. The process of claim 14, wherein the ketones are methyl vinyl ketone and ethyl vinyl ketone.

16. A process for producing a renewable biofuel from a liquid bio-oil or pyrolysis oil, the process comprising:
(a) subjecting a liquid bio-oil or pyrolysis oil feedstream to a separation in a fractionator to produce a stream having the boiling point of naphtha;
(b) subjecting the naphtha stream and at least a portion of a liquid bio-oil or pyrolysis oil stream containing carbonyl oxygenates to a carbon-carbon bond forming condensation reaction in a catalytic distillation column to form $C_6+$ enriched condensates, wherein the oxygenates are selected from the group consisting of $C_3$ oxygenates, $C_4$ oxygenates and $C_5$ oxygenates and mixtures thereof;
(c) contacting the bio-oil or pyrolysis oil containing condensates of step (a) with hydrogen and hydrotreating the condensates to form a hydrotreated feedstream; and
(d) fractionating the hydrotreated bio-oil or pyrolysis oil to obtain a $C_6+$ renewable biofuel, wherein the condensation reaction in step (a) and the hydrotreating in step (b) occurs in the distillation column.

17. The process of claim 16, wherein the feedstream containing carbonyl oxygenates originates from an aqueous stream removed from a solids separator.

18. The process of claim 16, wherein prior to step (a):
(i) biomass is converted in a biomass conversion reactor into gaseous, liquid and solid components;
(ii) the gaseous components and solid components are separated from the liquid components;
(iii) the liquid components are separated into an aqueous phase and an organic stream containing $C_3$-$C_5$ oxygenates; and
(iv) the aqueous phase is then separated into another organic stream containing $C_3$-$C_5$ oxygenates.

19. The process of claim 16, wherein the feedstream containing carbonyl oxygenates originates from an aqueous stream removed from a solids separator.

20. The process of claim 16, wherein condensation occurs in a presence of a heterogeneous acid catalyst.

21. The process of claim 16, wherein the carbon-carbon bond forming condensation reaction is a Diels-Alder reaction, a Michael addition reaction or a Robinson annulation reaction.

22. The process of claim 16, wherein the carbon-carbon bond forming condensation reaction is an aldol condensation.

23. The process of claim 16, wherein the $C_3$ oxygenates, $C_4$ oxygenates and $C_5$ oxygenates are selected from the group consisting of carboxylic acids, carboxylic acid esters, ketones and aldehydes.

24. A process for producing a renewable biofuel from liquid pyrolysis oil, the process comprising:
(a) subjecting a liquid pyrolysis oil feedstream containing carbonyl oxygenates to a carbon-carbon bond forming condensation reaction to form $C_6+$ enriched condensates, wherein the oxygenates are selected from the group consisting of $C_3$ oxygenates, $C_4$ oxygenates, $C_5$ oxygenates and mixtures thereof, and further wherein the $C_3$, $C_4$ and $C_5$ oxygenates are selected from the group consisting of carboxylic acids, carboxylic acid esters, ketones and aldehydes;
(b) contacting the pyrolysis oil containing condensates of step (a) with hydrogen and hydrotreating the condensates to form a hydrotreated bio-oil comprising $C_6+$ hydrocarbons; and
(c) fractionating the hydrotreated pyrolysis oil to obtain a $C_6+$ renewable biofuel, wherein the condensation reaction in step (a) and the hydrotreating in step (b) occurs in the same reactor.

25. The process of claim 24, wherein prior to step (a):
(i) biomass is converted in a biomass conversion reactor into gaseous, liquid and solid components;
(ii) the gaseous components and solid components are separated from the liquid components;
(iii) the liquid components are separated into an aqueous phase and an organic stream containing $C_3$-$C_5$ oxygenates; and
(iv) the aqueous phase is then separated into another organic stream containing $C_3$-$C_5$ oxygenates.

* * * * *